US00PP12870P2

(12) United States Plant Patent
Henneke

(10) Patent No.: US PP12,870 P2
(45) Date of Patent: Aug. 20, 2002

(54) VIBURNUM PLANT NAMED 'HENNEKE'

(75) Inventor: Rodney Henneke, Milan, IN (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 09/765,454

(22) Filed: Jan. 22, 2001

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—June Hwu
(74) *Attorney, Agent, or Firm*—C. A. Whealy

(57) ABSTRACT

A distinct cultivar of Viburnum plant named 'Henneke', characterized by its upright and rounded plant habit; very freely branching, dense and bushy plant habit; durable foliage that is relatively less susceptible to marginal scorching; numerous small white flowers arranged in large rounded hemispherical cymes; long-persisting dark red fruit; and superior winter hardiness; plants have been observed to tolerate temperatures as low as −35° C.

1 Drawing Sheet

BACKGROUND OF THE INVENTION

The present Invention relates to a new and distinct cultivar of Viburnum plant, botanically known as *Viburnum dilatatum*, and hereinafter referred to by the cultivar name Henneke.

The new Viburnum is a product of a breeding program conducted by the Inventor in Milan, Ind. The objective of the breeding program was to create new Viburnum cultivars with excellent winter hardiness.

The new Viburnum originated from a cross by the Inventor of two unidentified selections of *Viburnum dilatatum*, not patented. The cultivar Henneke was discovered and selected by the Inventor in the spring of 1990 as a single plant within the progeny of the stated cross in a controlled environment in Milan, Ind., on the basis of its winter hardiness.

Asexual reproduction of the new cultivar by softwood cuttings taken at Milan, Ind., since 1993, has shown that the unique features of this new Viburnum are stable and reproduced true to type in successive generations.

SUMMARY OF THE INVENTION

Plants of the cultivar Henneke have not been observed under all possible environmental conditions. The phenotype may vary somewhat with variations in environment such as temperature, light intensity, daylength, irrigation amount and frequency, and fertilizer type and rate without, however, any variance in genotype.

The following traits have been repeatedly observed and are determined to be the unique characteristics of 'Henneke'. These characteristics in combination distinguish 'Henneke' as a new and distinct cultivar:

1. Upright and rounded plant habit.
2. Very freely branching; dense and bushy plant habit.
3. Durable foliage that is relatively less susceptible to marginal scorching.
4. Numerous small white flowers arranged in large rounded hemispherical cymes.
5. Long-persisting dark red fruit; fruit persists until late spring.

6. Superior winter hardiness; plants have been observed to tolerate temperatures as low as −35° C.

Plants of the new Viburnum can be compared to plants of the *Viburnum dilatatum* cultivar Erie, not patented. In side-by-side comparisons conducted in Grand Haven, Mich., plants of the new Viburnum differ from plants of the cultivar Erie in the following characteristics:

1. Plants of the new Viburnum are not as upright as plants of the cultivar Erie.
2. Plants of the new Viburnum are more freely branching than plants of the cultivar Erie.
3. Plants of the new Viburnum have more durable foliage that is less susceptible to marginal scorching than plants of the cultivar Erie.
4. Cymes of the new Viburnum are rounded and hemispherical in shape whereas cymes of the cultivar Erie are flat-topped.
5. Plants of the new Viburnum are significantly more winter hardy than plants of the cultivar Erie as plants of the cultivar Erie die-back when exposed to temperatures of −15° C.

Plants of the new Viburnum can be compared to plants of the *Viburnum dilatatum* cultivar Michael Dodge, not patented. In side-by-side comparisons conducted in Grand Haven, Mich., plants of the new Viburnum differ from plants of the cultivar Michael Dodge in the following characteristics:

1. Plants of the new Viburnum are not as upright as plants of the cultivar Michael Dodge.
2. Plants of the new Viburnum are more freely branching than plants of the cultivar Michael Dodge.
3. Fruit color of the new Viburnum is dark red whereas fruit color of the cultivar Michael Dodge is light green.
4. Cymes of the new Viburnum are hemispherical in shape whereas cymes of the cultivar Michael Dodge are flat-topped.
5. Plants of the new Viburnum are significantly more winter hardy than plants of the cultivar Michael Dodge as plants of the cultivar Michael Dodge die-back when exposed to temperatures of −15° C.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Viburnum.

The photograph at the top of the sheet comprises a side perspective view of a typical flowering plant of 'Henneke'.

The photograph at the bottom of the sheet comprises a close-up view of typical fruits of 'Henneke'. Plants used for the photographs were about four years old.

DETAILED BOTANICAL DESCRIPTION

In the following description, color references are made to The Royal Horticultural Society Colour Chart except where general terms of ordinary dictionary significance are used. Plants were grown in Grand Haven, Mich. under outdoor field conditions which closely approximate commercial production conditions. Plants used for the description were about four years old.

Botanical classification: *Viburnum dilatatum* cultivar Henneke.

Parentage:

*Male, or pollen, parent.*—Unidentified *Viburnum dilatatum* selection, not patented.

*Female, or seed, parent.*—Unidentified *Viburnum dilatatum* selection, not patented.

Propagation:

*Type cutting.*—By softwood cuttings.

*Time to initiate roots.*—About 25 days at 32° C.

*Time to produce a rooted cutting or liner.*—About 65 days at 32° C.

*Root description.*—Freely branching, fibrous.

Plant description:

*Crop time.*—From rooted liners, about one growing season is required to produce a flowering finished plant in a one-gallon container.

*Form.*—Upright and rounded plant habit; uniform; dense and bushy perennial shrub.

*Usage.*—Appropriate for one to three-gallon containers.

*Plant height, soil level to top of plant plane.*—About 2 to 3 m.

*Plant width.*—About 2 to 3 m.

*Branching habit.*—When pinched, very freely branching with about 32 lateral branches per plant.

*Lateral branches.*—Length: About 34.3 cm. Diameter: About 7.5 mm. Internode length: About 8.5 cm. Texture: Pubescent. Color: 197B.

*Lenticels.*—Brown in color and less than 1 mm in diameter.

*Foliage description.*—Leaves simple, opposite, generally symmetrical and long persisting. Tolerant to stresses; relatively less susceptible to marginal scorching. Deciduous. Quantity per lateral branch: Typically about 23. Length: About 9 cm. Width: About 6.5 cm. Shape: Broadly ovate. Apex: Acute to obtuse. Base: Obtuse to rounded. Margin: Undulate. Texture: Pubescent; slightly rugose. Color: Young foliage, upper surface: 137B. Young foliage, lower surface: 137C. Mature foliage, upper surface: 137B; venation, 137B. Mature foliage, lower surface: 137C; venation, 193B. Petiole: Length: About 1 cm. Diameter: About 2.5 mm. Color: 193B.

Flower description:

*Flower type and habit.*—Small single rounded flowers arranged on terminal hemispherical or dome-shaped cymes. Flowers not persistent. Flowers not fragrant.

*Natural flowering season.*—Continuously flowering May through June in Grand Haven, Mich.

*Flower longevity.*—Individual flowers last about 4 weeks on the plant.

*Quantity of flowers.*—Freely flowering with about 294 flowers per cyme and about 1 to 5 cymes per lateral branch.

*Cyme diameter.*—About 10 cm.

*Cyme length.*—About 6.5 cm.

*Flower buds.*—Length: About 1 cm. Diameter: About 7.5 mm. Shape: Ovate. Color: 141A.

*Petals.*—Arrangement: Single whorl of five petals, fused, rotate. Length: About 4 mm. Width: About 3.5 mm. Shape: Obovate. Apex: Obtuse. Margin: Entire. Color: When opening, upper and lower surfaces: White, 155A. Fully opened, upper and lower surfaces: White, 155D, becoming brown, 177A with subsequent development.

*Calyx.*—Shape: Star; five-toothed. Sepal shape: Acute; apex, acute; margin, entire. Color: Green, close to 141A. Size: Less than 1 mm in length and less than 1 mm in diameter.

*Pedicels.*—Angle: About 80° from vertical. Strength: Strong. Length: About 5 to 25 mm. Color: 141A.

*Reproductive organs.*—Stamens: Quantity of stamens per flower: Five. Anther length: Less than 1 mm. Anther color: 160D. Pollen amount: Scarce. Pollen color: 160D. Pistils: Pistil quantity per flower: One. Pistil length: Less than 1 mm. Stigma shape: Three-lobed. Stigma color: Gray. Style length: Less than 1 mm.

*Fruit.*—Type: Drupe. Length: About 5.5 mm. Diameter: About 5.5 mm. Shape: Broadly ovate. Color: Dark red, 46A to 46B. Longevity: Persists until May in Grand Haven, Mich.

*Seed.*—Quantity per fruit: One. Length: About 3.5 mm. Diameter: About 1.75 mm. Shape: Oval. Color: Golden yellow, 22A.

Disease resistance: Under commercial production conditions, plants of the new Viburnum have not been observed to be resistant to pathogens common to Viburnum.

Low temperature tolerance: Plants of the new Viburnum have been observed to tolerate temperatures as low as −35° C.

It is claimed:

1. A new and distinct cultivar of Viburnum plant named 'Henneke', as illustrated and described.

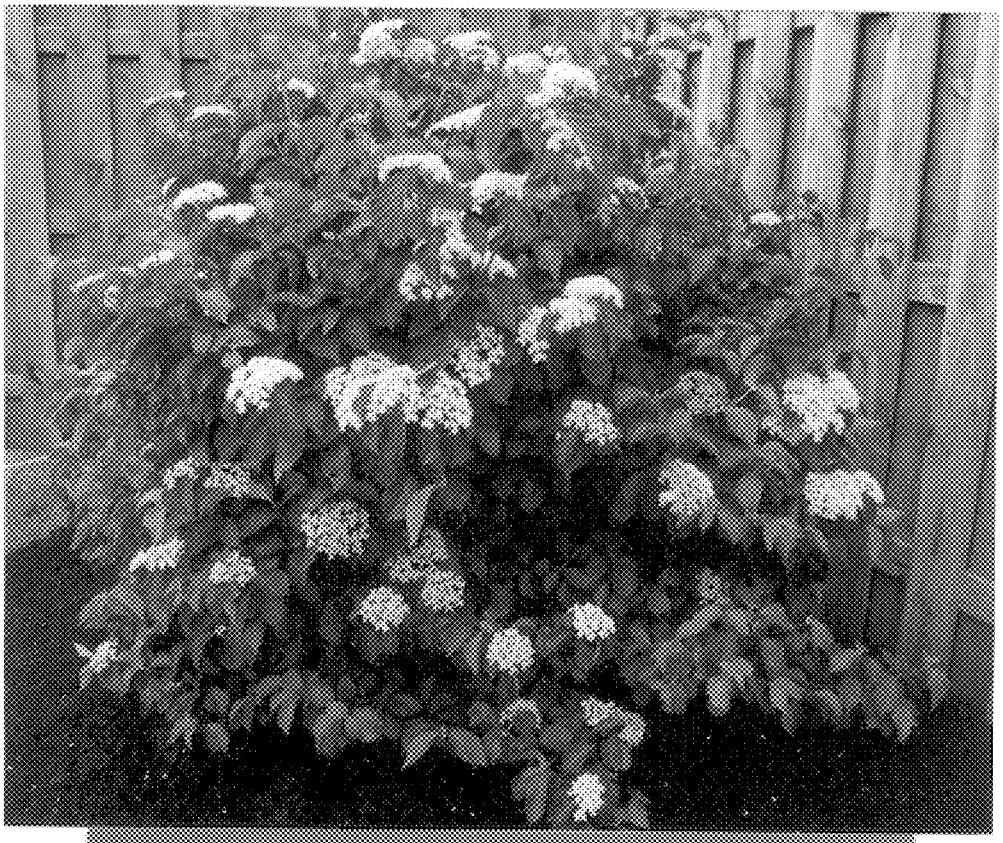
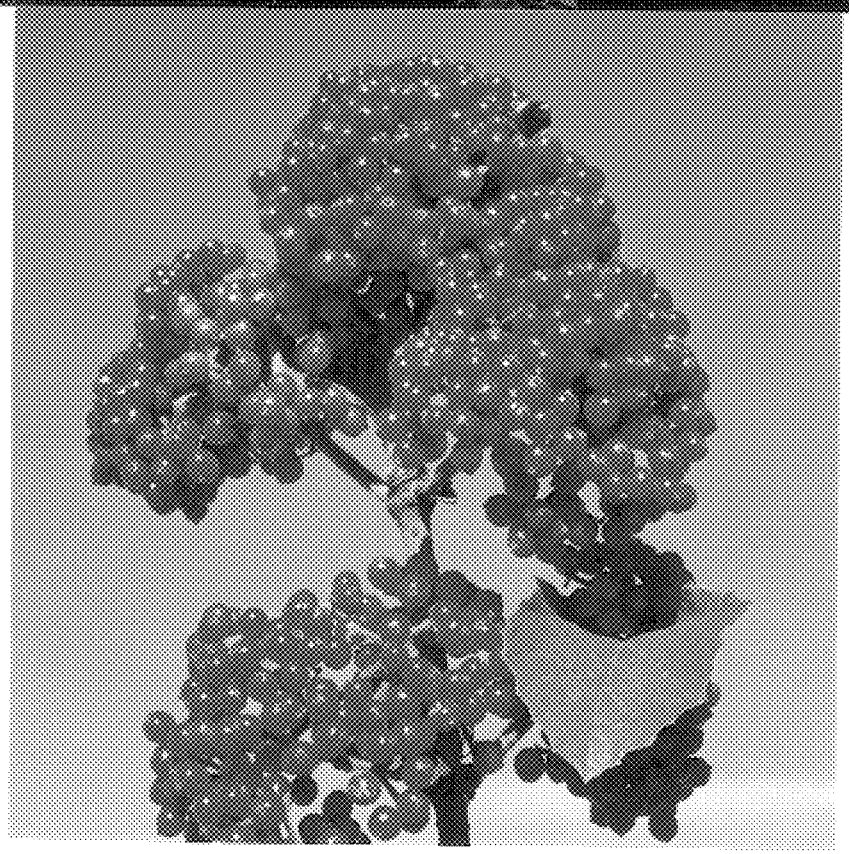

* * * * *